United States Patent [19]

Beaver

[11] Patent Number: 5,352,335
[45] Date of Patent: Oct. 4, 1994

[54] GROUNDWATER TREATMENT PROCESS

[75] Inventor: Phillip R. Beaver, Baton Rouge, La.

[73] Assignee: Albemarle Corporation, Richmond, Va.

[21] Appl. No.: 973,972

[22] Filed: Nov. 9, 1992

[51] Int. Cl.$^5$ .................... B01D 3/10; B01D 3/34; C02F 1/04

[52] U.S. Cl. .................... 203/11; 95/159; 95/149; 202/182; 202/183; 202/205; 203/42; 203/49; 203/92; 203/96; 210/750; 210/908

[58] Field of Search .................... 203/11, 10, 49, 92, 203/14, 96, 42; 202/202, 182, 183, 205; 570/262; 261/136, 147; 210/664, 737

[56] References Cited

U.S. PATENT DOCUMENTS

| | | | |
|---|---|---|---|
| 1,836,563 | 12/1931 | Webster et al. | |
| 1,866,417 | 7/1932 | Mackert . | |
| 2,141,349 | 12/1938 | Engelhardt | 23/206 |
| 2,143,223 | 1/1939 | Heath | 23/217 |
| 2,278,999 | 4/1942 | Kuhl | 183/114.6 |
| 2,339,386 | 1/1944 | Edwards | 210/122.5 |
| 2,367,384 | 1/1945 | Tynstra et al. | 210/1 |
| 2,372,540 | 3/1945 | Balcar | 202/49 |
| 2,409,691 | 10/1946 | Noble | 196/8 |
| 2,527,444 | 10/1950 | Pape | 210/26 |
| 2,565,568 | 8/1951 | McCants | 202/40 |
| 2,773,003 | 12/1956 | Brown et al. | 196/1 |
| 2,927,075 | 3/1960 | Brown | 208/208 |
| 2,930,753 | 3/1960 | McMahon | 210/21 |
| 2,935,452 | 5/1960 | LaFrance et al. | 202/46 |
| 2,937,142 | 5/1960 | Rios | 210/40 |
| 2,943,703 | 7/1960 | Thayer | 183/115 |
| 2,999,808 | 9/1961 | Brown | 208/264 |
| 3,054,653 | 9/1962 | Barton et al. | 23/2 |
| 3,140,244 | 7/1964 | Simek et al. | 202/46 |
| 3,326,778 | 6/1967 | Mock | 202/234 |
| 3,337,422 | 8/1967 | Colton | 203/36 |
| 3,344,583 | 10/1967 | Styring et al. | 55/44 |
| 3,448,042 | 6/1969 | Mattia et al. | 210/26 |
| 3,475,282 | 10/1969 | Hamilton | 203/49 |
| 3,527,699 | 9/1970 | King | 216/21 |
| 3,528,284 | 9/1970 | Skoglund et al. | 73/104 |
| 3,597,167 | 8/1971 | Marks et al. | 23/306 |
| 3,617,209 | 11/1971 | Massone et al. | 23/154 |
| 3,690,040 | 9/1972 | Halfon | 55/46 |
| 3,803,030 | 4/1974 | Montanaro et al. | 210/26 |
| 3,847,570 | 11/1974 | Gunther | 95/163 |
| 3,876,508 | 4/1975 | Bonnema et al. | 203/35 |
| 3,884,650 | 5/1975 | Woerner et al. | 55/54 |
| 3,884,768 | 5/1975 | Griffith | 203/11 |
| 3,898,058 | 8/1975 | McGill | 55/50 |
| 3,904,518 | 9/1975 | Hutton et al. | 210/11 |
| 3,931,001 | 1/1976 | Winn | 210/22 |
| 3,958,964 | 5/1976 | Koch | 55/186 |
| 3,977,966 | 8/1976 | Pradt et al. | 210/17 |
| 3,986,953 | 10/1976 | Beaucaire | 210/43 |
| 4,066,514 | 1/1978 | Fowler | 203/11 |
| 4,069,148 | 1/1978 | Hutton et al. | 210/11 |
| 4,072,604 | 2/1978 | Ward | 208/341 |
| 4,080,287 | 3/1978 | Conway et al. | 210/7 |
| 4,110,370 | 8/1978 | Engelbach et al. | 260/530 N |
| 4,162,902 | 7/1979 | Wiesner et al. | 55/54 |
| 4,167,973 | 9/1979 | Forte et al. | 166/267 |
| 4,201,665 | 5/1980 | Savage et al. | 210/32 |
| 4,236,973 | 12/1980 | Robbins | 203/10 |
| 4,412,924 | 11/1983 | Feather | 210/744 |
| 4,495,056 | 1/1985 | Venardos et al. | 208/11 R |
| 4,510,242 | 4/1985 | Tedder | 435/157 |
| 4,517,094 | 5/1985 | Beall | 210/664 |
| 4,518,503 | 5/1985 | Fermaglich | 210/662 |

(List continued on next page.)

OTHER PUBLICATIONS

Thibodeaux, Louis J., "Air Stripping of Organics from Wastewater. A Compendium", Proceedings of the National Conference on Complete Water Use, 2nd *Water's Interface with Energy, Air and Solids,* Chicago, Ill., May 4–8, 1975, Publ. by AICHE, New York, N.Y., 1976, pp. 358–378.

*Primary Examiner*—Virginia Manoharan
*Attorney, Agent, or Firm*—E. E. Spielman, Jr.

[57] ABSTRACT

A continuous process for the extraction of halogenated hydrocarbons from a dilute, halogenated hydrocarbon-containing aqueous fluid, in high efficiency, while dramatically reducing the stripping medium requirement for the extraction and without substantially increasing the amount of halogenated hydrocarbons discharged to the atmosphere.

19 Claims, 1 Drawing Sheet

U.S. PATENT DOCUMENTS

| | | | |
|---|---|---|---|
| 4,522,730 | 6/1985 | Hochgesand et al. | 95/159 |
| 4,534,869 | 8/1985 | Seibert | 210/788 |
| 4,539,077 | 9/1985 | Jonckers et al. | 203/49 |
| 4,544,488 | 10/1985 | O'Brien | 210/664 |
| 4,589,896 | 5/1986 | Chen et al. | 62/28 |
| 4,595,461 | 6/1986 | Jeromin et al. | 203/72 |
| 4,608,163 | 8/1986 | Yohe et al. | 210/150 |
| 4,623,464 | 11/1986 | Ying et al. | 210/616 |
| 4,626,354 | 12/1986 | Hoffman et al. | 210/603 |
| 4,640,743 | 2/1987 | Bannon et al. | 203/87 |
| 4,659,343 | 4/1987 | Kelly | 55/16 |
| 4,670,028 | 6/1987 | Kennedy | 55/48 |
| 4,670,278 | 6/1987 | Healey et al. | 426/387 |
| 4,676,908 | 6/1987 | Ciepiela et al. | 210/638 |
| 4,713,089 | 12/1987 | Robbins | 203/26 |
| 4,713,343 | 12/1987 | Wilson, Jr. et al. | 435/264 |
| 4,755,304 | 7/1988 | Hallberg et al. | 210/747 |
| 4,758,346 | 7/1988 | Johnson | 210/638 |
| 4,764,272 | 8/1988 | Fox, Sr. | 210/104 |
| 4,783,242 | 11/1988 | Robbins | 203/87 |
| 4,801,384 | 1/1989 | Steiner | 210/634 |
| 4,846,934 | 7/1989 | Carberry | 202/177 |
| 4,871,450 | 10/1989 | Goodrich et al. | 210/151 |
| 4,886,603 | 12/1989 | Taylor | 210/641 |
| 4,892,664 | 1/1990 | Miller | 210/747 |
| 4,902,310 | 2/1990 | Vara et al. | 55/46 |
| 4,909,947 | 3/1990 | Johnson et al. | 210/737 |
| 4,966,654 | 10/1990 | Carberry | 202/177 |
| 4,978,518 | 12/1990 | Lesher et al. | 423/504 |
| 5,037,551 | 8/1991 | Barkley et al. | 210/603 |
| 5,039,423 | 8/1991 | Kelley | 210/664 |
| 5,069,796 | 12/1991 | Fox | 210/664 |
| 5,106,507 | 4/1992 | Von Klock et al. | 210/664 |

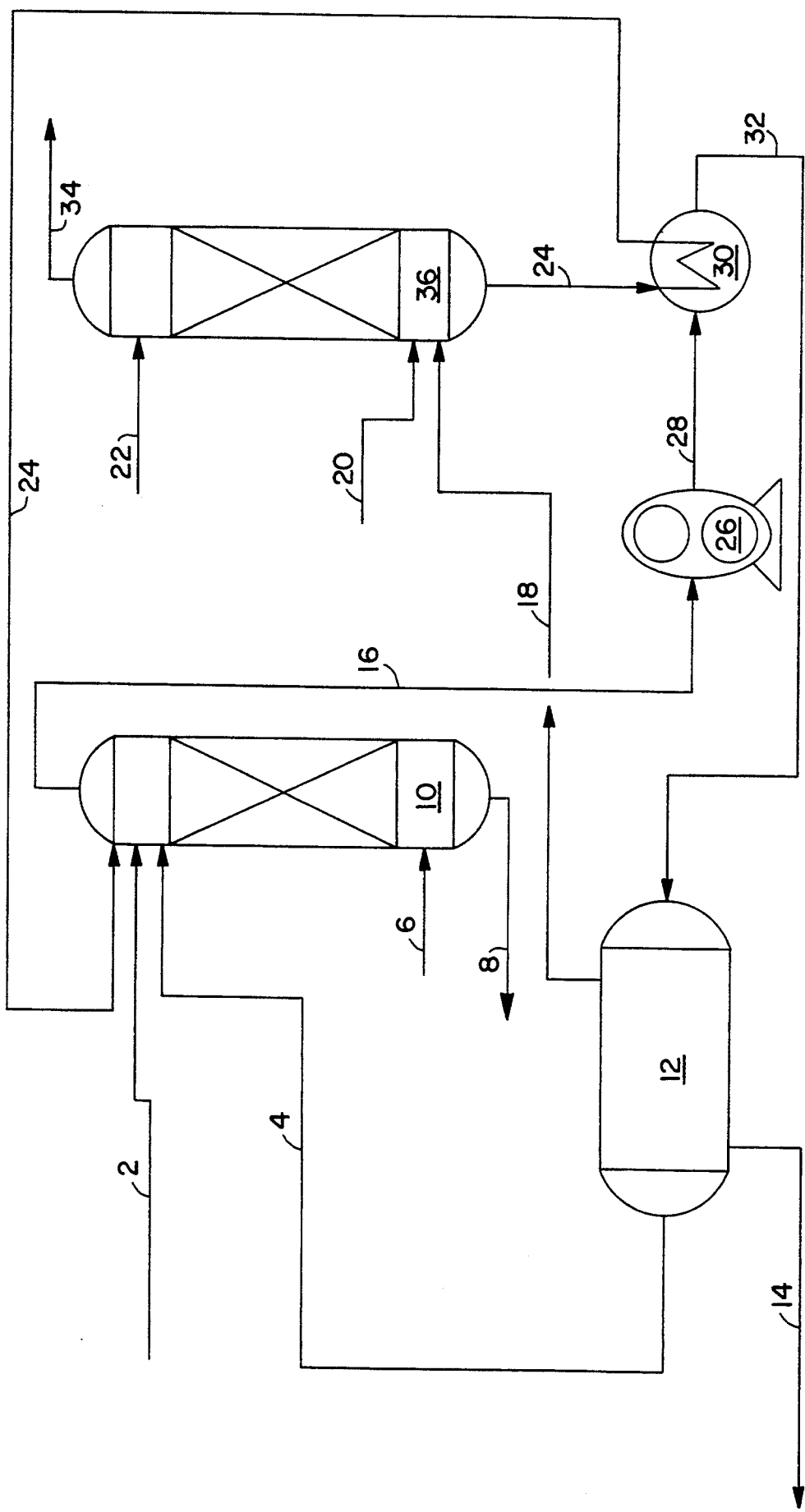

GROUNDWATER TREATMENT PROCESS

BACKGROUND

This invention relates to a novel process for removing halogenated hydrocarbons from dilute, halogenated hydrocarbon-containing aqueous fluids. More particularly, this invention relates to a novel process for removing trace amounts of halogenated hydrocarbons, such as 1,2-dichloroethane, 1,1-dichloroethane, 1,1,2,2-perchloroethylene, 1,1,2-trichloroethane, ethylene dibromide, methylene bromide and the like from contaminated ground water.

Methods for the removal of trace hydrocarbons from aqueous and vapor streams are extensive and vary widely. For example, U.S. Pat. No. 4,495,056 teaches steam stripping, carbon adsorption, biological treatment, and activated sludge treatment to purify water. Beall, U.S. Pat. No. 4,517,094, teaches adsorption of organic contaminants on two media: (1) organoclay and (2) granulated carbon. Von Klock et al., U.S. Pat. No. 5,106,507, utilize a stripping gas and a bed of activated carbon to remove hydrocarbon contaminants. Miller, U.S. Pat. No. 4,892,664, provides a method for decontaminating water which is contaminated by small concentrations of dissolved volatile organic compounds, the method comprising introducing the contaminated water into an air stripping column wherein the contaminants are stripped with air, pretreating the organic compounds-carrying air in a preheater, and passing the heated air through a catalytic stage that oxidized the organic compounds. U.S. Pat. No. 4,544,488 discloses the use of an induced draft air stripper and carbon adsorption bed to remove volatile organic chemical from water.

Carberry, U.S. Pat. No. 4,846,934 and U.S. Pat. No. 4,966,654 discloses a system for removing hydrocarbon contaminants from groundwater and moisture-laden soil. The system of Carberry comprises a steam stripping tower which is operated at subatmospheric pressure, a series of condensers and separators, and finally a carbon adsorber to remove any remaining uncondensed hydrocarbon contaminants.

Robbins, U.S. Pat. No. 4,236,973, utilizes a vapor such as air or steam to strip organic contaminants having a boiling point in excess of 200° C. from pH adjusted water. Once stripped, the stripping vapor and organic contaminants can be passed into a scrubber wherein the vapor and contaminants are contacted with a stream of caustic or other material which preferentially absorbs the contaminants from the vapor.

Robbins, U.S. Pat. No. 4,783,242, describes a distillation system for removing vaporizable components from an aqueous medium comprising: a distillation column using steam to vaporize the vaporizable components, a condenser means to condense at least a portion of the vapor from the distillation column, a separator means to separate vapor from a recirculated fluid in the separator means, and a thermal compressor means to remove vapors from the separator means and inject motive steam into the column. According to Robbins, the vaporizable components include trichloroethane, propylene chlorohydrin, bromine, methylene chloride, benzene, toluene, and mixtures thereof.

McGill, U.S. Pat. No. 3,898,058, provides a process for removal of hydrocarbons by the application of a vacuum to a contacting vessel in which a contaminated water stream is caused to flow across packing material or trays for efficient gas removal. The removed hydrocarbon materials are then compressed, condensed and further separated to remove gaseous and/or liquid hydrocarbons from the system.

While the foregoing provide a multitude of methods for removal of contaminants from groundwater, there continues to be a need for efficient, yet cost effective means for reducing groundwater contaminants while at the same time reducing the amount of contaminants discharged to the atmosphere.

SUMMARY OF THE INVENTION

This invention provides, inter alia, a process for the extraction of halogenated hydrocarbons from a dilute, halogenated hydrocarbon-containing aqueous fluid, in high efficiency, while dramatically reducing the stripping medium requirement for the extraction and without substantially increasing the amount of halogenated hydrocarbons discharged to the atmosphere. Remarkably, the purposes of this invention are accomplished without the need for a carbon adsorption system to remove trace halogenated organics from the stripping medium used to extract the halogenated hydrocarbons from the aqueous fluid. Thus, the purchase and/or regeneration of a carbon adsorption bed, or alternate means of adsorption, is avoided.

Accordingly, in one embodiment, this invention provides a process for substantially reducing the amount of halogenated hydrocarbons in a dilute, halogenated hydrocarbon-containing aqueous fluid. The process comprises: (a) introducing dilute, halogenated hydrocarbon-containing aqueous fluid into an upper portion of an upright enclosed chamber; (b) introducing a stripping medium into a lower portion of the chamber whereby the stripping medium intimately contacts the dilute, halogenated hydrocarbon-containing aqueous fluid in a countercurrent manner; (c) removing halogenated hydrocarbon-depleted aqueous fluid from the lower portion of the chamber; (d) removing halogenated hydrocarbon rich vapor stream from the upper portion of the chamber; (e) condensing at least a portion of the halogenated hydrocarbon rich vapor stream thereby forming a halogenated hydrocarbon rich liquid; and (f) contacting a non-condensed portion of the halogenated hydrocarbon rich vapor stream with an absorbing fluid whereby the amount of halogenated hydrocarbons in the contacted non-condensed portion is reduced by at least about 85 wt. % based on the initial weight of halogenated hydrocarbons in the non-condensed portion.

Not only does this invention provide a facile economic means for removal of hydrocarbons from dilute aqueous streams using a stripping medium, it also provides a means for removal of about 85 to about 99 wt. % or more of the hydrocarbons which may be present in the stripping medium prior to discharge of stripping medium to the atmosphere. Accordingly, the process of this invention may be used to reduce the level of hydrocarbons in groundwater without substantially increasing the amount of hydrocarbons discharged to the atmosphere.

BRIEF DESCRIPTION OF THE DRAWING

The FIGURE is a schematic diagram, not to scale, of apparatus and process for continuous extraction of halogenated hydrocarbons from an aqueous stream.

DESCRIPTION OF THE PREFERRED EMBODIMENTS

In a preferred embodiment, the process of this invention features an energy efficient continuous process for substantially reducing the amount of halogenated hydrocarbons in a dilute, halogenated hydrocarbon-containing aqueous fluid. The process comprises: (a) continuously introducing dilute, halogenated hydrocarbon-containing aqueous fluid into an upper portion of an upright, elongated, enclosed chamber containing contact packing material; (b) continuously introducing steam into a lower portion of the enclosed chamber below the contact packing whereby the steam contacts the dilute, halogenated hydrocarbon-containing aqueous fluid in a countercurrent manner within the enclosed chamber; (c) continuously removing halogenated hydrocarbon-depleted aqueous fluid from the lower portion of the enclosed chamber; (d) continuously removing a vapor stream containing halogenated hydrocarbon and steam from the upper portion of the enclosed chamber; (e) continuously condensing at least a portion of the halogenated hydrocarbon and steam in the vapor stream from the upper portion of the enclosed chamber thereby forming a halogenated hydrocarbon-rich liquid form; and (f) continuously contacting a non-condensed portion of the vapor stream from the upper portion of the enclosed chamber with an absorbing fluid whereby the amount of halogenated hydrocarbon in the vapor stream is substantially reduced.

Accordingly, this invention utilizes conventional apparatus connected by conventional piping and conduits. However, the invention provides a novel combination of conventional apparatus which is utilized in a unique process to obtain unexpected results.

For the purposes of this invention, the terms "dilute, halogenated hydrocarbon-containing aqueous fluid" and/or "contaminated ground water" define aqueous mediums containing an amount of halogenated hydrocarbon compound(s) within the range of from about 0.1 ppm to saturation at about 9000 ppm or more. "Halogenated hydrocarbon-depleted aqueous fluid" as used herein means aqueous fluid in which the organic contaminants have been substantially reduced.

In many areas of the United States, ground water may be contaminated by trace amounts of organic compounds. While this invention may be applicable to the removal of any organic contaminants from groundwater, it is particularly useful in removing halogenated hydrocarbons such as 1,2-dichloroethane, 1,1-dichloroethane, 1,1,2,2-dichloroethylene, 1,2-dichlorothylene, carbon tetrachloride, perchlorethylene, trichlorothylene, 1-1-dichloroethane, 1,1,2-trichloroethane, chloroform, 1-chloro-2-bromopropane, 1,4-dichlorobutane, 1,2,3,4-tetrachlorobutane, 1,1,1,2,2,2-hexachloroethane, 1,1,1,2-tetrachloroethane, 1,1,2,2-tetrachloroethylene, hexachlorobutadiene, pentachlorobutadiene, tetrachlorobenzene, pentachlorobenzene, hexachlorobenzene, methylene bromide, ethylene dibromide, and the like. The amount of halogenated organic compounds in the ground water can vary widely with proximity to the originating source. Generally, the groundwater will contain less than 1 wt. % organic contaminants and usually less than 9,000 ppm organic contaminants.

Initially, halogenated hydrocarbon-containing aqueous fluid is desirably treated to remove any entrained solids and/or oily residue which may be present in the aqueous stream. Then the solids free dilute, halogenated hydrocarbon-containing aqueous fluid is introduced into the upper portion of an upright enclosed chamber.

The enclosed chamber may be an empty vessel, however, it is highly preferred that the vessel contain packing material or distributor trays for providing intimate contact between the contaminated groundwater and the stripping medium. For purposes of this invention, the enclosed chamber containing packing material and/or distributor trays will be referred to hereinafter as a "stripping column". When packing material is used, it is highly desirable that the packing material be inert to halogenated hydrocarbons and stripping medium with which it comes in contact. Suitable packing material may consist of beads, saddles, pellets, rods, and the like which are formed from plastics, ceramic, metals, clays, silicas, or other inert materials, with ceramic saddles being particularly preferred.

The stripping column desirably contains internal fluid distribution conduits located above and below the packed section. The stripping column may also contain a demister for reducing the carryover of entrained fluid out of the stripping column in the gas or vapor stream. The design of such a stripping column for contact between a stripping medium and the aqueous fluid is well within the skill of those in the art. Thus, any suitable upright stripping column may be used provided there is sufficient contact between the aqueous fluid and stripping medium to remove more than about 85 weight percent of halogenated hydrocarbons from the aqueous fluid.

In order to reduce the amount of halogenated hydrocarbons in the aqueous fluid, a stripping medium is introduced into the lower portion of the stripping column so that the stripping medium contacts the aqueous fluid in a countercurrent manner. Suitable stripping media include air, steam, carbon dioxide, argon, nitrogen, helium, and the like. It is particularly preferred to use steam when the contaminants are halogenated hydrocarbons since steam can be condensed thereby limiting the potential for atmospheric pollution.

Once contacted, a halogenated hydrocarbon-rich vapor stream is removed from the upper portion of the stripping column and a halogenated hydrocarbon-depleted aqueous fluid is removed from the lower portion of the stripping column. It is preferred that the halogenated hydrocarbon-depleted fluid contain less than about 10 ppm of halogenated hydrocarbons, more preferably less than about 1 ppm halogenated hydrocarbons, and most preferably from about 0.01 to about 0.2 ppm halogenated hydrocarbons or lower, depending on the volume of the halogenated hydrocarbon-depleted fluid removed from the lower portion of the stripping column.

The halogenated hydrocarbon rich vapor stream exiting the upper portion of the stripping column is then fed to a condenser whereby at least a portion of the halogenated hydrocarbon rich vapor stream is condensed thereby forming an aqueous phase, an organic phase, and a non-condensed portion. The aqueous phase may still contain a low level of halogenated hydrocarbon due to the solubility of halogenated hydrocarbons in water. Hence, this aqueous phase is typically recycled to the stripping column for further removal of contaminants. The organic phase will contain a substantial amount of halogenated hydrocarbons which are removed from the dilute, halogenated hydrocarbon-containing aqueous fluid. This organic stream may be collected and sold, burned, or otherwise disposed of.

The non-condensed portion of the halogenated hydrocarbon-rich vapor stream is then fed to a second enclosed chamber whereby it is contacted with an absorbing fluid in a countercurrent manner thereby removing halogenated hydrocarbons from the non-condensed portion. Thus, the discharge to the atmosphere from the second enclosed chamber is essentially free of halogenated hydrocarbons. By the term "essentially free" is meant that more than about 85 wt. %; more preferably, more than about 95 wt. %; and most preferably, more than about 99 wt. % of the halogenated hydrocarbons initially present in the non-condensed portion are removed by the absorber fluid. Accordingly, there is little need to utilize subsequent adsorption means such as carbon adsorption or activated clays for removal of halogenated hydrocarbons which may be present in the non-condensed portion. In a particularly preferred embodiment, the absorber fluid is collected from the bottom portion of the second enclosed chamber and fed to the stripping column for removal of halogenated hydrocarbons from the absorber fluid.

The absorber fluid is typically an aqueous fluid which may contain a low level of halogenated hydrocarbons. By "low level" is meant less than about 100 ppm, most preferably about 50 ppm or less halogenated hydrocarbons. When the absorber fluid is pure water, e.g. water containing undetectable limits of halogenated hydrocarbons, the discharge of halogenated hydrocarbons to the atmosphere from the second enclosed chamber may be essentially zero, i.e. the level of halogenated hydrocarbons remaining in the non-condensed portion exiting the upper portion of the second enclosed chamber is undetectable by conventional means such as gas chromatographic analysis, infrared spectroscopy, nuclear magnetic resonance and the like.

In yet another embodiment, the vents from storage tanks containing halogenated hydrocarbons, or dilute, halogenated hydrocarbon-containing aqueous fluids, may also be fed to the second enclosed chamber before discharge of the tank vents to the atmosphere. Such storage tank vents may contain halogenated hydrocarbon vapors depending on the concentration of halogenated hydrocarbons in the stored fluids, their vapor pressure, and the temperature of the storage tanks. In some cases, such as when the storage tanks are located at a distance from the second chamber, a third chamber may be used in series or parallel with the second chamber for absorbing hydrocarbons from the tanks' vent stream.

In a particularly preferred embodiment, the stripping column for contact of the stripping medium and dilute, halogenated hydrocarbon-containing aqueous fluid is operated under subatmospheric pressure. Preferably the pressure of the stripping column is in the range of from about 1 mm Hg to about 600 mm Hg, and most preferably, from about 20 mm Hg to about 200 mm Hg. The optimum reduced pressure within the stripping column is that pressure which is sufficient to effectively strip a major portion of the halogenated hydrocarbons from the aqueous fluid at the desired temperature. In general, a reduced pressure of about 40 mm Hg to about 160 mm Hg and more often from about 60 mm Hg to about 120 mm Hg gives good results.

The halogenated hydrocarbon-containing aqueous fluid fed to the stripping column is typically operated at ambient temperature. In general, the temperature of the halogenated hydrocarbon-containing aqueous fluid obtained from containment wells is in the range of 0° to 40° C. It is highly preferred that the absorber fluid used in the second enclosed chamber be as cool as practical. Typically the operating temperature of the second enclosed chamber ranges from about 20° to about 30° C. for groundwater absorber fluids.

The present invention stripping column, which is operated under subatmospheric conditions, can be constructed of any material which can withstand the subatmospheric conditions without collapsing and which is not adversely affected by contact with halogenated compounds, organic or inorganic. Such materials as metals or metal alloys (e.g. titanium, tantalum, carbon steel, and nickel alloys), carbon steel lined with acid brick, rubber, thermoplastic and the like are suitable. Especially useful materials of construction are carbon steel or reinforced plastics such as fiberglass reinforced plastics (e.g., fiberglass reinforced polyester) and carbon fiber reinforced plastics (e.g., graphite fiber reinforced polyester). These materials should be rated to withstand full service vacuum at temperatures up to 120° C. for short periods of time. However, in normal operations, operating temperatures will typically be about 30° C. or lower with an operating pressure near 40 mm Hg. In the most preferred embodiment, carbon steel is the material of choice for subatmospheric pressure operation.

DETAILED DESCRIPTION OF THE DRAWINGS

Having described the process of the invention, reference is now made to FIG. 1. Dilute, halogenated hydrocarbon-containing aqueous fluid 2 is fed to the upper portion of stripping column 10 which preferably contains contact packing. Stripping medium 6 is fed to the lower portion of stripping column 10 whereby it contacts aqueous fluid 2 in a counter-current manner in the contact packing. It is particularly desirable to feed aqueous fluid 2 into the stripping column at a point above the contact packing, and to feed the stripping medium 6 into the stripping column at a point below the contact packing.

Halogenated hydrocarbon-depleted aqueous fluid 8 is removed from the bottom portion of stripping column 10 whereby it may be disposed of as a non-hazardous stream. In the preferred embodiment, aqueous fluid 8 is at a temperature which avoids thermal pollution, e.g. in the range 20° C. to 50° C. Halogenated hydrocarbon rich vapor 16 is removed from the top portion of stripping column 10 by vacuum forming device 26 (which device may be a vacuum pump, direct contact condenser and vacuum pump, or steam jet ejector) which provides a subatmospheric pressure in stripping column 10. The discharge stream 28 from vacuum forming device 26 is fed to condenser 30 which cools the halogenated hydrocarbon rich vapor stream sufficiently to allow formation of cooled stream 32 containing an aqueous phase, an organic phase, and a non-condensed portion. The coolant for condenser 30 may be selected from a wide range of materials which can provide sufficient cooling of discharge stream 28 so that a condensed portion of stream 28 is formed. Such fluids may include stream 24, described below, which is the discharge liquid stream from absorbing column 36.

Cooled stream 32 is fed to phase separator 12 wherein halogenated hydrocarbon organic stream 14 is separated from aqueous stream 4 containing a minor amount of halogenated hydrocarbons and a non-condensable vapor stream 18 containing a minor amount of halogenated hydrocarbons and stripping medium. By "minor amount" is meant less than about 40 wt. % of the total weight of the vapor and liquid stream 32.

Non-condensable vapor stream 18 is then fed to the bottom portion of second enclosed chamber 36 wherein it is contacted in a countercurrent manner with absorber fluid 22 which may be pure water or an aqueous source having a low level of halogenated hydrocarbon contaminants such as halogenated hydrocarbon-depleted stream 8 which is fed to the upper portion of second enclosed chamber 36. In a preferred embodiment, various storage tank vent streams 20 containing halogenated hydrocarbon vapors may also be fed to the lower portion of second enclosed chamber 36 for removal of trace amounts of halogenated hydrocarbons. Stream 34 exiting the top portion of second enclosed chamber 36 is essentially free of halogenated hydrocarbons and may be safely vented to the atmosphere. Liquid stream 24 exiting the bottom portion of second enclosed chamber 36 contains halogenated hydrocarbons and therefore it is preferably treated for removal of halogenated hydrocarbons by recycle to stripping column 10. Since liquid stream 24 is typically cooler than stream 28 exiting vacuum forming device 26, it may be practical to utilize stream 24 to condense at least a portion of the halogenated hydrocarbon rich vapor stream 28 in condenser 30.

In order to further illustrate the invention, the following example is given. This example should not be construed as limiting the invention in any way.

EXAMPLE

Contaminated groundwater (170 liters per minute at 4°-32° C. and containing 1000 ppm of halogenated hydrocarbons principally 1,2-ethylene dichloride) is fed into the upper portion of stripping column 10 containing contact packing. Steam (45 to 365 kilograms per hour) is fed into the lower portion of stripping column 10 below the contact packing. Stream 8 exiting the bottom of stripping column 10 contains 0.05 ppm halogenated hydrocarbons at a flow rate of 360 liters per minute. Exiting the top of stripping column 10 is a halogenated hydrocarbon rich vapor stream 16 containing 12 kilograms of halogenated hydrocarbons and 48 kilograms of steam which is fed to vacuum pump 26 and partial condenser 30. Cooled stream 32 exiting partial condenser 30 contains 3.4 liters per minute mixed aqueous phase and organic phase, and 1.13 cubic meters per minute non-condensable phase which are then fed to phase separator 12 wherein 3.37 liters per minute organic phase containing 98 wt % halogenated organics is removed. The aqueous stream 4 (0.4 liters per minute containing 9000 ppm halogenated organics is recycled to stripping column 10. Non-condensable stream 18 containing 1360 grams per hour of air and 454 grams per hour of halogenated hydrocarbons is fed to second enclosed chamber 36 wherein it is contacted with 189 liters per minute of water containing 50 ppm of halogenated hydrocarbons. Also entering the bottom of the second enclosed chamber 36 is 250 grams per hour of halogenated hydrocarbons and 4.5 kilograms per hour of air from various storage tank vent streams. Exiting the bottom of second enclosed chamber 36 is liquid stream 24 (189 liters per minute) containing 112.5 ppm halogenated hydrocarbons. Exiting the top of second enclosed chamber 36 is vapor stream 34 containing about 5 grams per hour of halogenated hydrocarbons. If pure water is used as the absorber fluid 22, vapor stream 34 exiting the top of scrubbing column 36 contains no detectible amount of halogenated hydrocarbons. The stripping column 10 is operated at about 30° C. and 31 mm Hg, and the second enclosed chamber 36 is operated at about 21° to 24° C. and 760 mm Hg.

The process is very energy efficient in light of the fact that the amount of steam required to operate the process at subatmospheric pressure is much less than that which would be required to operate the same process at atmospheric pressure because of the reduced equilibrium temperature of the dilute, halogenated hydrocarbon-containing fluid at the reduced pressure. Accordingly, the present process and apparatus provides a means of conserving energy when recovering halogenated hydrocarbon from dilute, halogenated hydrocarbon-containing aqueous fluids.

Variations of the invention are within the spirit and scope of the appended claims.

What is claimed is:

1. A carbon adsorption-free process for extracting halogenated hydrocarbons from a dilute, halogenated hydrocaron-containing aqueous fluid, said process comprising:
   (a) introducing dilute, halogenated hydrocarbon-containing aqueous fluid into an upper portion of an upright enclosed chamber;
   (b) introducing a stripping medium into a lower portion of the chamber whereby the stripping medium intimately contacts the dilute, halogenated hydrocarbon-containing aqueous fluid in a countercurrent manner;
   (c) removing halogenated hydrocarbon-depleted aqueous fluid from the lower portion of the chamber;
   (d) removing a halogenated hydrocarbon rich vapor stream from the upper portion of the chamber;
   (e) condensing at least a portion of the halogenated hydrocarbon-rich vapor stream thereby forming a halogenated hydrocarbon-rich liquid portion and a halogenated hydrocarbon-containing non-condensed portion;
   (f) contacting at least a portion of the non-condensed portion with an aqueous absorbing fluid whereby the amount of halogenated hydrocarbons in the contacted non-condensed portion is reduced by at least about 85 wt. % based on the initial weight of halogenated hydrocarbons in the non-condensed portion; and
   (g) collecting contacted absorbing fluid from step (f) and introducing collected fluid into the upright enclosed chamber.

2. The process of claim 1 wherein said stripping medium is steam.

3. The process of claim 2 wherein said halogenated hydrocarbon is a chlorinated or brominated hydrocarbon.

4. The process of claim 3 wherein said halogenated hydrocarbon is predominantly 1,2-dichloroethane.

5. The process of claim 3 wherein said halogenated hydrocarbon is predominantly ethylene dibromide.

6. The process of claim 1 wherein the stripping medium is steam and wherein the dilute, halogenated hydrocarbon-containing aqueous fluid and steam are contacted under subatmospheric pressure.

7. The process of claim 6 wherein said dilute, halogenated hydrocarbon-containing aqueous fluid is introduced into said chamber at a temperature in the range of from about 0° to about 40° C.

8. The process of claim 7 wherein the subatmospheric pressure within the chamber is in the range of from about 20 to about 200 mm Hg.

9. The process of claim 6 wherein the subatmospheric pressure within the chamber is in the range of from about 1 to about 600 mm Hg.

10. The process of claim 1 wherein said dilute, halogenated hydrocarbon-containing aqueous fluid is introduced into said enclosed chamber at a temperature in the range of from about 0° to about 40° C.

11. The process of claim 10 wherein the subatmospheric pressure within the chamber is in the range of from about 60 to about 120 mm Hg.

12. A carbon adsorption-free continuous process for extracting halogenated hydrocarbons from a dilute, halogenated hydrocarbon-containing aqueous fluid, said process comprising:
   (a) continuously introducing dilute, halogenated hydrocarbon-containing aqueous fluid into an upper portion of an upright, elongated, enclosed chamber containing contact packing material;
   (b) continously introducing steam into a lower portion of the enclosed chamber below the contact packing whereby the steam contacts the dilute, halogenated hydrocarbon-containing aqueous fluid in a countercurrent manner within the enclosed chamber;
   (c) continously removing a halogenated hydrocarbon-depleted aqueous fluid from the lower portion of the enclosed chamber;
   (d) continously removing a vapor stream containing halogenated hydrocarbon and steam from the upper portion of the enclosed chamber;
   (e) continuously condensing at least a portion of the halogenated hydrocarbon and steam in the vapor stream from the upper portion of the enclosed chamber thereby forming a halogenated hydrocarbon rich liquid portion and a non-condensed portion;
   (f) continously contacting at least a portion of the non-condensed portion with an aqueous absorbing fluid whereby the amount of halogenated hydrocarbon is contacted non-condensed portion is reduced by at least about 85wt. % based on the initial weight of halogenated hydrocarbons in the non-condensed portion; and
   (g) collecting contacted absorbing fluid from step (f) and introducing collected fluid into the upright enclosed chamber.

13. The process of claim 12 wherein said halogenated hydrocarbon is a brominated or chlorinated hydrocarbon.

14. The process of claim 13 wherein said chlorinated hydrocarbon is predominantly 1,2-dichloroethane.

15. The process of claim 13 wherein said brominated hydrocarbon is predominantly ethylene dibromide.

16. The process of claim 12 wherein dilute, halogenated hydrocarbon-containing aqueous fluid and steam are contacted under subatmospheric pressure.

17. The process of claim 16 wherein said dilute, halogenated hydrocarbon-containing aqueous fluid is introduced into said enclosed chamber at a temperature in the range of from about 0° to about 40° C.

18. The process of claim 17 wherein the subatmospheric pressure within the enclosed chamber is in the range of from about 40 to about 120 mm Hg.

19. The process of claim 17 wherein said dilute, halogenated hydrocarbon-containing aqueous fluid is introduced into said enclosed chamber at a temperature in the range of from about 0° to about 40° C.

* * * * *

UNITED STATES PATENT AND TRADEMARK OFFICE
CERTIFICATE OF CORRECTION

PATENT NO. : 5,352,335

DATED : October 4, 1994

INVENTOR(S) : Phillip R. Beaver

It is certified that error appears in the above-identified patent and that said Letters Patent is hereby corrected as shown below:

On the title page:
Item[56]. References Cited, U.S. Patent Documents, Line 7, reads "... Tynstra et al. ..." and should read -- ... Tymstra et al. ... --.

Column 10, Line 1, reads "steam ... " and should read -- stream ... --.

Column 10, Line 8 reads "carbon is contacted ... " and should read -- carbon in the contacted ... --.

Column 10, Line 33 reads "... claim 17 ..." and should read -- ... claim 12 ... --.

Signed and Sealed this

Seventh Day of March, 1995

BRUCE LEHMAN

Attest:

Attesting Officer

Commissioner of Patents and Trademarks